(12) United States Patent
Hyodo

(10) Patent No.: US 11,020,039 B2
(45) Date of Patent: Jun. 1, 2021

(54) EVOKED POTENTIAL MEASURING APPARATUS

(71) Applicant: NIHON KOHDEN CORPORATION, Tokyo (JP)

(72) Inventor: Akira Hyodo, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 184 days.

(21) Appl. No.: 15/436,910

(22) Filed: Feb. 20, 2017

(65) Prior Publication Data

US 2017/0245775 A1    Aug. 31, 2017

(30) Foreign Application Priority Data

Feb. 26, 2016    (JP) .............................. JP2016-035795

(51) Int. Cl.
| | | |
|---|---|---|
| *A61B 5/0484* | (2006.01) | |
| *A61B 5/04* | (2006.01) | |
| *A61B 5/0402* | (2006.01) | |
| *A61B 5/00* | (2006.01) | |
| *A61B 5/377* | (2021.01) | |

(Continued)

(52) U.S. Cl.
CPC .............. *A61B 5/377* (2021.01); *A61B 5/316* (2021.01); *A61B 5/318* (2021.01); *A61B 5/7214* (2013.01); *A61B 5/7235* (2013.01)

(58) Field of Classification Search
None
See application file for complete search history.

(56) References Cited

U.S. PATENT DOCUMENTS 5,601,091 A * 2/1997 Dolphin ............. A61B 5/04845
                                                           600/544
5,638,825 A    6/1997 Yamazaki et al.
(Continued)

FOREIGN PATENT DOCUMENTS

JP    H07-289529 A    11/1995
JP    H10-80409 A     3/1998
(Continued)

OTHER PUBLICATIONS

Extended European Search Report issued in Patent Application No. 17 15 6848 dated Jun. 26, 2017.
(Continued)

*Primary Examiner* — Patrick Fernandes
*Assistant Examiner* — Benjamin S Melhus
(74) *Attorney, Agent, or Firm* — Pearne & Gordon LLP

(57) ABSTRACT

An evoked potential measuring apparatus includes: an evoked potential acquiring section which is configured to acquire a plurality of evoked potential waveforms from a subject in response to stimulation; an average processing section which is configured to arithmetically average the plurality of evoked potential waveforms to acquire an average waveform; a first statistical value calculator which, each time a waveform set including an N (N is 2 or more) number of evoked potential waveforms is acquired, is configured to calculate a first statistical value of the waveform set; and an updation processing section which is configured to update the average waveform to eliminate a waveform set in which the first statistical value exceeds a first threshold, from the arithmetic average.

7 Claims, 6 Drawing Sheets

(51) Int. Cl.
*A61B 5/316* (2021.01)
*A61B 5/318* (2021.01)

(56) References Cited

U.S. PATENT DOCUMENTS

| | | | |
|---|---|---|---|
| 5,697,379 A | 12/1997 | Neely | |
| 6,196,977 B1* | 3/2001 | Sininger | A61B 5/04845 |
| | | | 600/545 |
| 6,331,164 B1* | 12/2001 | Shaw | A61B 5/121 |
| | | | 600/559 |
| 7,014,613 B2* | 3/2006 | John | A61B 5/04845 |
| | | | 600/559 |
| 7,133,715 B1* | 11/2006 | Smits | A61B 5/04845 |
| | | | 600/544 |
| 8,177,726 B2* | 5/2012 | John | A61B 5/121 |
| | | | 600/559 |
| 2003/0225340 A1* | 12/2003 | Collura | A61B 5/0482 |
| | | | 600/545 |
| 2004/0204659 A1* | 10/2004 | John | A61B 5/04845 |
| | | | 600/559 |
| 2008/0262371 A1* | 10/2008 | Causevic | A61B 5/04017 |
| | | | 600/544 |
| 2011/0040202 A1 | 2/2011 | Luo et al. | |
| 2011/0196615 A1* | 8/2011 | Vitali | G06K 9/0051 |
| | | | 702/19 |
| 2011/0224570 A1* | 9/2011 | Causevic | G06K 9/00543 |
| | | | 600/544 |
| 2013/0266163 A1 | 10/2013 | Morikawa et al. | |
| 2013/0324880 A1 | 12/2013 | Adachi et al. | |
| 2014/0195202 A1 | 7/2014 | Ishiguro et al. | |
| 2015/0065813 A1* | 3/2015 | Wochlik | A61B 5/04845 |
| | | | 600/301 |
| 2016/0045751 A1* | 2/2016 | Jiang | A61B 5/0488 |
| | | | 607/59 |
| 2017/0245776 A1* | 8/2017 | Kurtz | A61B 5/0484 |

FOREIGN PATENT DOCUMENTS

| | | |
|---|---|---|
| JP | H10-286244 A | 10/1998 |
| JP | 2842409 B2 | 1/1999 |
| JP | H11-004815 A | 1/1999 |
| JP | 2001-231767 A | 8/2001 |
| JP | 2004-216184 A | 8/2004 |
| JP | 2014-132928 A | 7/2014 |
| WO | 2012-151498 A2 | 11/2012 |
| WO | 2013-001836 A1 | 1/2013 |

OTHER PUBLICATIONS

Japanese Office action issued in Patent Application No. 2016-035795 dated Jan. 7, 2020.

* cited by examiner

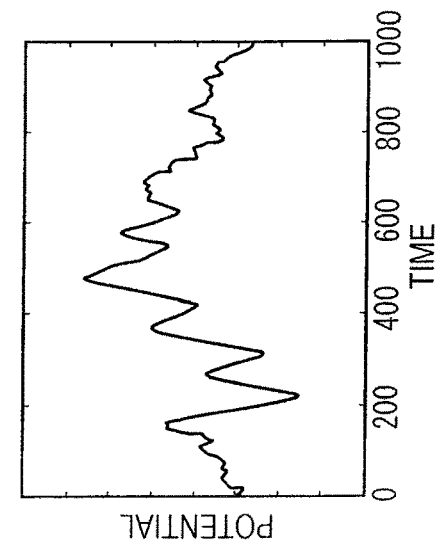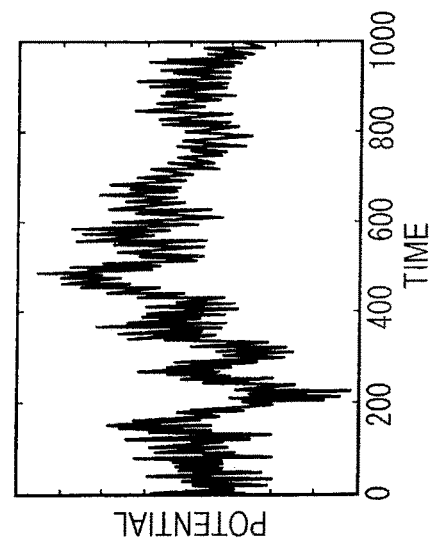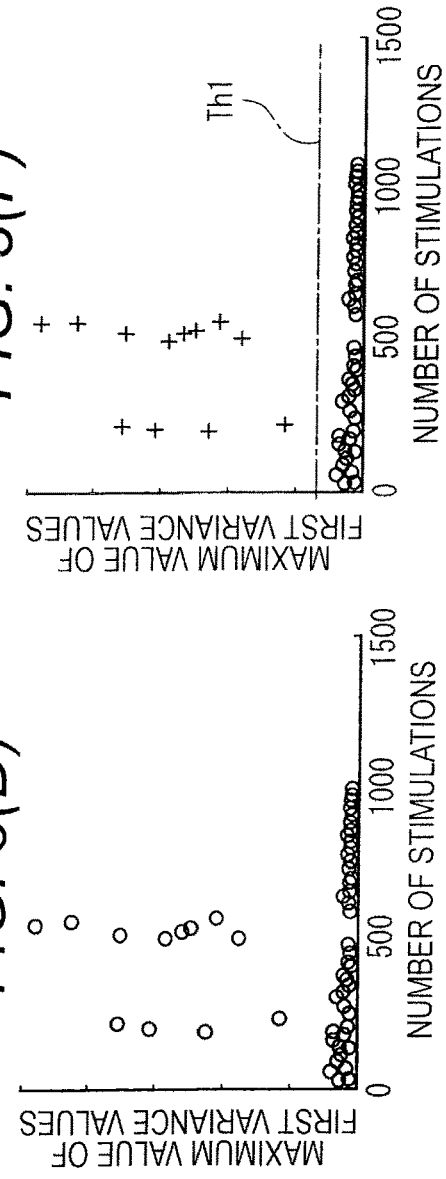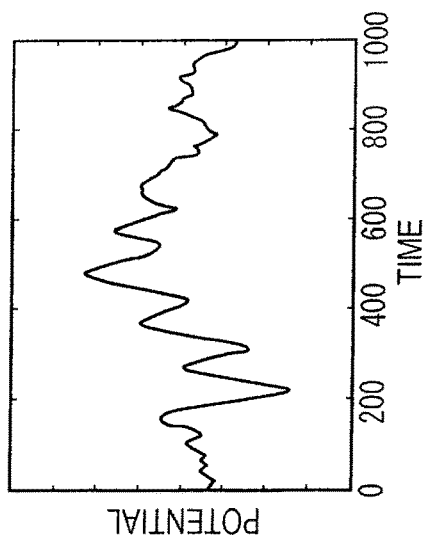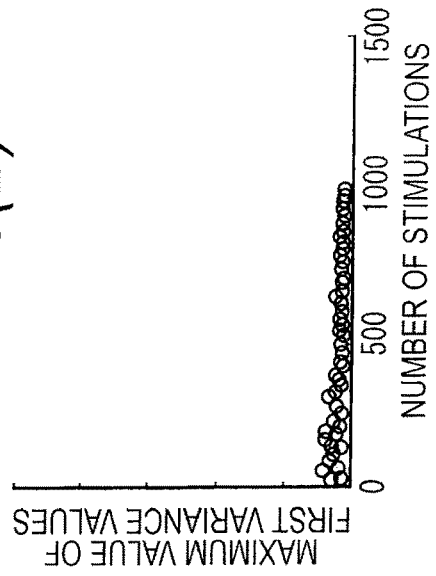

EVOKED POTENTIAL MEASURING APPARATUS

CROSS-REFERENCE TO RELATED APPLICATION(S)

This application is based upon and claims the benefit of priority from prior Japanese patent application No. 2016-035795, filed on Feb. 26, 2016, the entire contents of which are incorporated herein by reference.

BACKGROUND

The presently disclosed subject matter relates to an apparatus for measuring an evoked potential. An evoked potential means a transient potential variation which appears in the brain waves and myopotential of the subject in response to nerve stimulation.

Japanese Patent No. 2,842,409 discloses an apparatus of this type. In the apparatus, a technique called "arithmetic average method" is employed. Specifically, a plurality of stimulations are repeatedly applied to the subject, and evoked potential waveforms which are obtained in response to the respective stimulations are added with reference to the stimulation timings. An average waveform is calculated by dividing the waveform which is obtained by the addition, by the number of additions. When such an average waveform is obtained, influences of electric/magnetic noises which are momentarily or constantly mixed into the waveforms can be eliminated, and a waveform which is approximated to the evoked potential waveform derived from the subject can be acquired.

In order to obtain a significant average waveform, stimulation is performed several hundreds to thousands of times. Therefore, the measurement is burdensome to the subject. Furthermore, there is a technique in which, in order to accurately perform such a measurement, noises of excessive amplitudes are detected, and the noises are automatically eliminated from the arithmetic average. However, not only noises of excessive amplitudes, but also environmental noises of a high frequency due to an electrocautery or the like, and noises of a low frequency due to large body motion may adversely affect the arithmetic average waveform.

SUMMARY

The presently disclosed subject matter may provide an evoked potential measuring apparatus which can perform highly accurately an evoked potential measurement in which the arithmetic average method is used, while the burden on the subject is reduced.

The evoked potential measuring apparatus may comprise: an evoked potential acquiring section which is configured to acquire a plurality of evoked potential waveforms from a subject in response to stimulation; an average processing section which is configured to arithmetically average the plurality of evoked potential waveforms to acquire an average waveform; a first statistical value calculator which, each time a waveform set including an N (N is 2 or more) number of evoked potential waveforms is acquired, is configured to calculate a first statistical value of the waveform set; and an updation processing section which is configured to update the average waveform to eliminate a waveform set in which the first statistical value exceeds a first threshold, from the arithmetic average.

BRIEF DESCRIPTION OF THE DRAWINGS

FIGS. 3(A) to 3(F) are views illustrating processes which are executed by the evoked potential measuring apparatus of FIG. 1.

DETAILED DESCRIPTION OF EXEMPLARY EMBODIMENTS

Embodiments will be described in detail with reference to the accompanying drawings.

Figure 1:
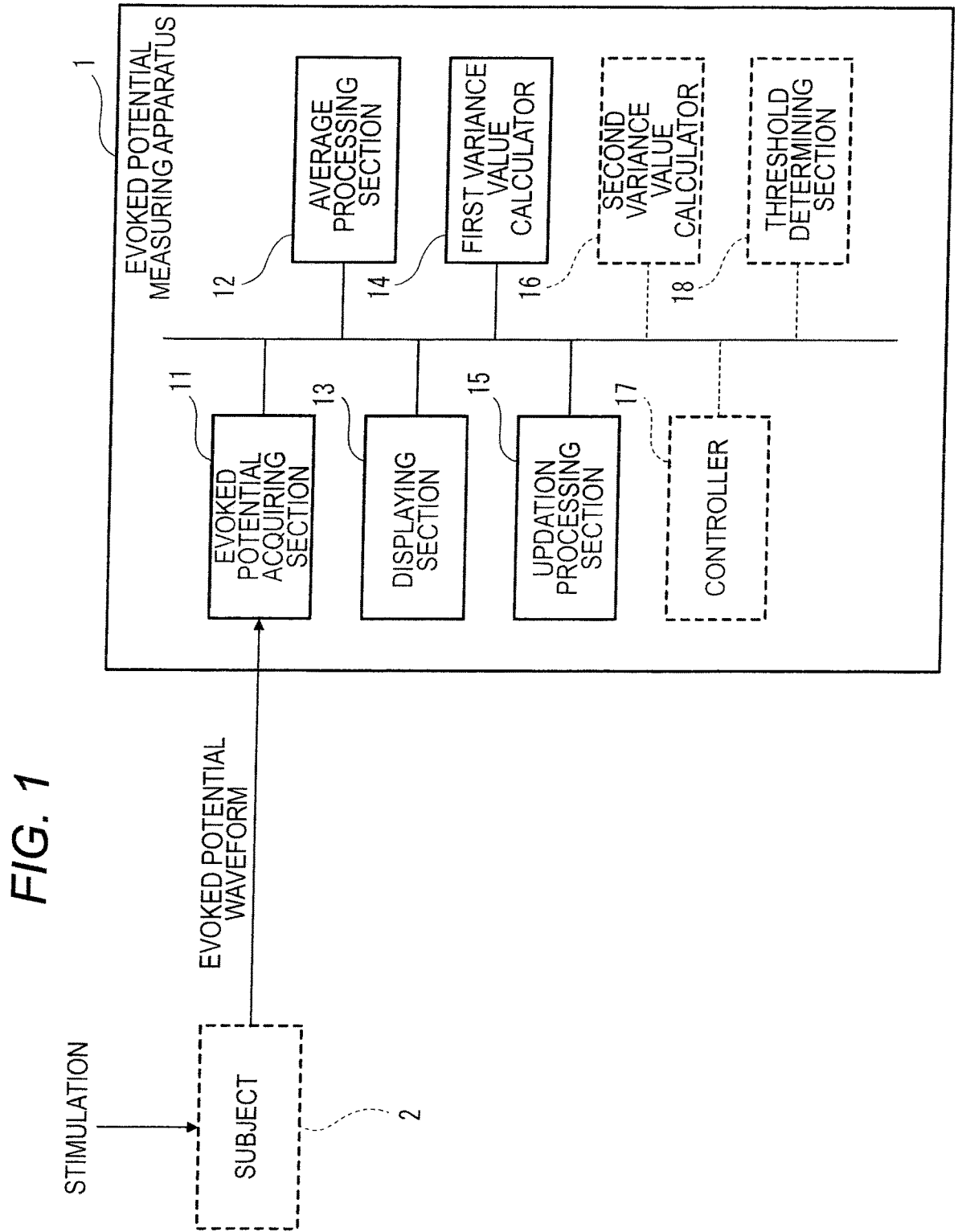
FIG. 1 is a block diagram illustrating the functional configuration of an evoked potential measuring apparatus of a first embodiment.

FIG. 1 is a block diagram illustrating the functional configuration of an evoked potential measuring apparatus 1 of a first embodiment. The evoked potential measuring apparatus 1 may include an evoked potential acquiring section 11, an average processing section 12, a displaying section 13, a first variance value calculator 14 (an example of the first statistical value calculator), and an updation processing section 15.

When stimulation is applied to a subject 2, an evoked potential waveform can be obtained. An evoked potential waveform shows a transient potential variation which appears in the brain waves and myopotential of the subject 2 as a response to the stimulation. Namely, an evoked potential waveform appears as a temporal change of the biopotential in which the timing of stimulation application is set as the reference timing.

Examples of stimulation are visual stimulation, auditory stimulation, electrical stimulation, and pain stimulation. Stimulation may be provided by an apparatus which is independent from the evoked potential measuring apparatus 1, or by a stimulation generator which is disposed in the evoked potential measuring apparatus 1, and which is not illustrated.

The evoked potential acquiring section 11 is configured so as to acquire evoked potential waveforms from the subject 2 in response to stimulation. The stimulation is repeatedly applied to the subject 2. Therefore, the evoked potential acquiring section acquires a plurality of evoked potential waveforms.

The average processing section 12 is configured so as to arithmetically average the plurality of evoked potential waveforms which are acquired by the evoked potential acquiring section 11, to acquire an average waveform. The displaying section 13 is configured so as to display the average waveform which is acquired by the average processing section 12.

The first variance value calculator 14 is configured so as to, each time a waveform set including an N number of evoked potential waveforms is obtained, calculate a variance value (first variance value, an example of the first statistical value) from variations of waveforms in the waveform set.

An integer of 2 or more may be adequately selected as N. Examples of N are 10, 25, and 50.

For example, the first variance value is calculated in the following manner. Each evoked potential waveform is expressed as a set of potential values at an X number of timings. For example, X is 1,000. A Y number of timings are selected from the X number of timings, and the variance values of potential values at the Y number of timings are calculated with respect to the N number of evoked potential waveforms. For example, Y is 10 or 100.

In the case where N is 25, X is 1,000, and Y is 10, each time 25 evoked potential waveforms are acquired with respect to 25 stimulations applied to the subject 2, the variance value of a waveform set including the 25 evoked potential waveforms is calculated. The potential values at 10 timings are selected from those at 1,000 timings constituting each of the evoked potential waveforms, and the variance values of the potential values at the selected timings are calculated with respect to the 25 evoked potential waveforms. Namely, the first variance value calculator 14 calculates 10 first variance values from one waveform set.

The updation processing section 15 is configured so as to determine whether the maximum value of the plurality of first variance values calculated by the first variance value calculator 14 exceeds a first threshold or not. If it is determined that the maximum value exceeds the first threshold, the updation processing section 15 updates the average waveform acquired by the average processing section 12 so as to eliminate a waveform set including such variance values from the arithmetic average. The updated average waveform is displayed on the displaying section 13.

Figure 2:
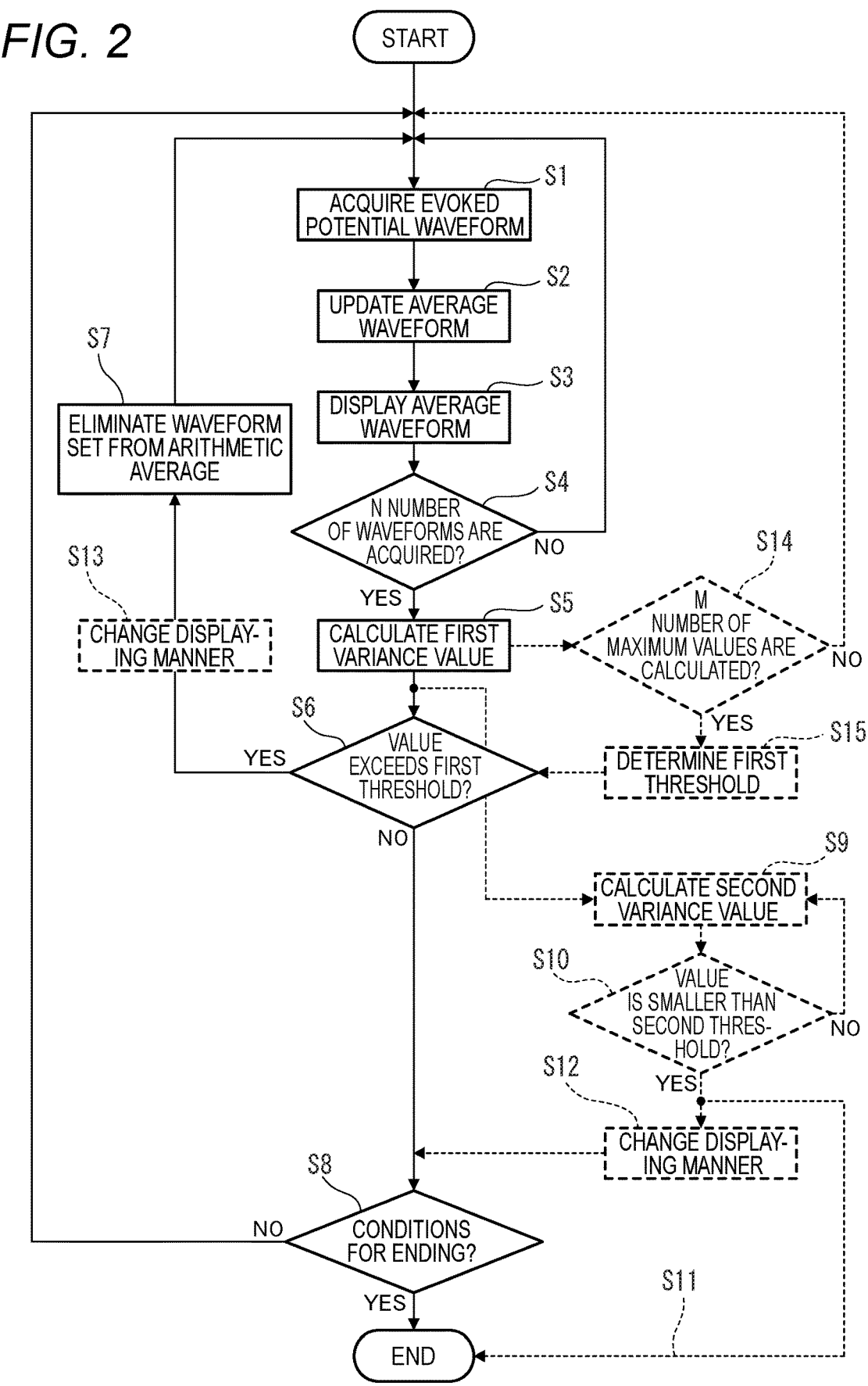
FIG. 2 is a flow chart illustrating processes which are executed by the evoked potential measuring apparatus of FIG. 1.

Next, the operation of the thus configured evoked potential measuring apparatus 1 will be described in detail with reference to FIGS. 2 to 3(F). FIG. 2 is a flow chart illustrating the operation of the evoked potential measuring apparatus 1.

When the measurement is started, the evoked potential acquiring section 11 acquires a first evoked potential waveform as a response to the first stimulation application (S1). Because of one evoked potential waveform, the average processing section 12 handles the evoked potential waveform acquired in step S1, as the average waveform (S2). The displaying section 13 displays the evoked potential waveform as the average waveform (S3).

Next, it is determined whether the predetermined number (N) of evoked potential waveforms constituting the waveform set have been acquired or not (S4). Here, one evoked potential waveform has been acquired (NO in step S4), and therefore the process returns to step S1. That is, the evoked potential acquiring section 11 acquires a second evoked potential waveform as a response to the second stimulation application (S1). The average processing section 12 arithmetically averages the two evoked potential waveforms to update the average waveform (S2). The displaying section 13 displays the updated average waveform (S3).

In the case where N is 10, the above-described process is repeated 10 times. In the tenth determination in step S4, 10 evoked potential waveforms have been acquired (YES in step S4), and therefore the first variance value calculator 14 calculates the first variance value with respect to the waveform set including the 10 evoked potential waveforms (S5).

As described above, potential values corresponding to the Y number of timings are selected from potential values corresponding to the X number of timings constituting each evoked potential waveform, and the variance values of the potential values at the Y number of timings are calculated with respect to 10 evoked potential waveforms. Namely, a Y number of first variance values are calculated with respect to the waveform set. For example, X is 1,000, and Y is 10.

Next, the updation processing section 15 determines whether the maximum value of the first variance values calculated by the first variance value calculator 14 exceeds the first threshold or not (S6).

FIG. 3(A) illustrates an average waveform which is obtained by arithmetically averaging about 1,000 evoked potential waveforms that are acquired with respect to about 1,000 stimulations. The abscissa indicates the time (which may be regarded as the number of timings). The ordinate indicates the potential. FIG. 3(B) illustrates a temporal change of the maximum value of the first variance values which are calculated for each waveform set including 10 evoked potential waveforms. The abscissa indicates the number of stimulations which are applied to the subject, and the ordinate indicates the maximum value of the first variance values.

The phenomenon has been described in which, when the arithmetic averaging is repeated, noises that are momentarily superimposed on the evoked potential waveforms can be eliminated. However, there is a case where sudden noises due to body motion, or electromyogram, an electrocautery, or the like cannot be eliminated by arithmetic averaging. FIG. 3(C) illustrates an average waveform which is obtained by arithmetically averaging about 1,000 evoked potential waveforms in the case where such noises are superimposed on the waveforms, and FIG. 3(D) illustrates a temporal change of the maximum value of first variance values that, in such a case, are acquired in a manner similar to that illustrated in FIG. 3(B). It can be seen that, in the vicinities of 250-th and 500-th stimulation applications, such noises are added, and the maximum value of the first variance values is extremely raised.

As seen from FIG. 3(C), in such a situation, even when about 1,000 arithmetic averaging processes are performed, noises remain to be superimposed on the average waveform, and it is difficult to read an evoked potential waveform derived from the subject. In order to obtain a waveform such as illustrated in FIG. 3(A), stimulation and arithmetic averaging must be further continued, and therefore a large burden is imposed on the subject.

As illustrated in FIG. 2, if it is determined that the maximum value of the first variance values calculated by the first variance value calculator 14 exceeds the first threshold (YES in step S6), the updation processing section 15 in the embodiment updates the average waveform so as to eliminate a waveform set containing the first variance values from the arithmetic average (S7).

In the case where a waveform set in which the maximum value of the first variance values is large to some extent is obtained, it is highly probable that, at the timing when the waveform set is obtained, noises which are hardly eliminated by arithmetic averaging are added to the waveform set. When such a waveform set remains as a component of the average waveform, a substantial time period is required to obtain a significant average waveform as illustrated in FIG. 3(C). In the embodiment, such a waveform set is eliminated from the arithmetic average, whereby the average waveform can be returned to the state attained before the problematic noises are mixed into the waveform.

As illustrated in FIG. 2, the process then returns to step S1, and the above-described processes are repeated in order to acquire the next waveform set. If it is determined that the maximum value of the first variance values calculated by the first variance value calculator 14 does not exceed the first threshold (NO in step S6), it is determined whether conditions for ending the process are satisfied or not (S8). Example of the ending conditions are that stimulation has been applied a predetermined number (for example, 3,000) of times (a predetermined number of evoked potential waveforms are acquired), and that a command for ending the measurement is input by the user.

If it is determined that the ending conditions are satisfied (YES in step S8), the evoked potential measurement is ended. If it is determined that the ending conditions are not satisfied (NO in step S8), the process returns to step S1, and the above-described processes are repeated in order to acquire the next waveform set.

FIG. 3(E) illustrates an average waveform which is obtained by arithmetically averaging about 1,000 evoked potential waveforms in the case where noises are added under the same conditions as those illustrated in FIG. 3(C) and FIG. 3(D), and the process in the embodiment is performed. FIG. 3(F) corresponds to FIG. 3(D), and illustrates a temporal change of the maximum value of the first variance values. In FIG. 3(F), the dash-dot line Th1 indicates the first threshold. Plots indicated by cross-like symbols show maximum values of the first variance values of the waveform sets in which the maximum values exceed the first threshold, and which are therefore eliminated from the arithmetic average. As seen from the comparison between FIG. 3(C) and FIG. 3(E), although the numbers of stimulations in FIG. 3(C) and FIG. 3(E) are approximately equal to each other, the waveform of FIG. 3(E) is obtained as a significant average waveform in which influences of environmental noises are eliminated, and which is equivalent to that illustrated in FIG. 3(A).

According to the configuration of the embodiment, therefore, influences of disturbance noises which are hardly coped by the related-art arithmetic average method can be eliminated by the relatively simple process. Consequently, the time period which elapses until a significant average waveform is obtained can be shortened, and namely the number of times when stimulation is applied to the subject 2 can be reduced. In an evoked potential measurement in which the arithmetic average method is used, therefore, the measurement can be performed highly accurately while the burden on the subject 2 is reduced.

As indicated by the broken lines in FIG. 1, the evoked potential measuring apparatus 1 may include a second variance value calculator 16 and a controller 17.

The second variance value calculator 16 is configured so as to calculate a variance value (second variance value, an example of the second statistical value) of the average waveform acquired by the average processing section 12.

For example, the second variance value is calculated in the following manner. An average waveform is expressed as a set of potential values at an X number of timings. For example, X is 1,000. A Y number of timings are selected from the X number of timings, and the variance values of potential values at the Y number of timings are calculated with respect to all evoked potential waveforms which have been added hitherto. For example, Y is 10 or 100.

The controller 17 is configured so as to determine whether the maximum value of the plurality of second variance values calculated by the second variance value calculator 16 is smaller than a predetermined second threshold or not. If it is determined that the maximum value is smaller than the second threshold, the controller 17 causes the acquisition of evoked potential waveforms by the evoked potential acquiring section 11, to be automatically stopped.

Figure 4:
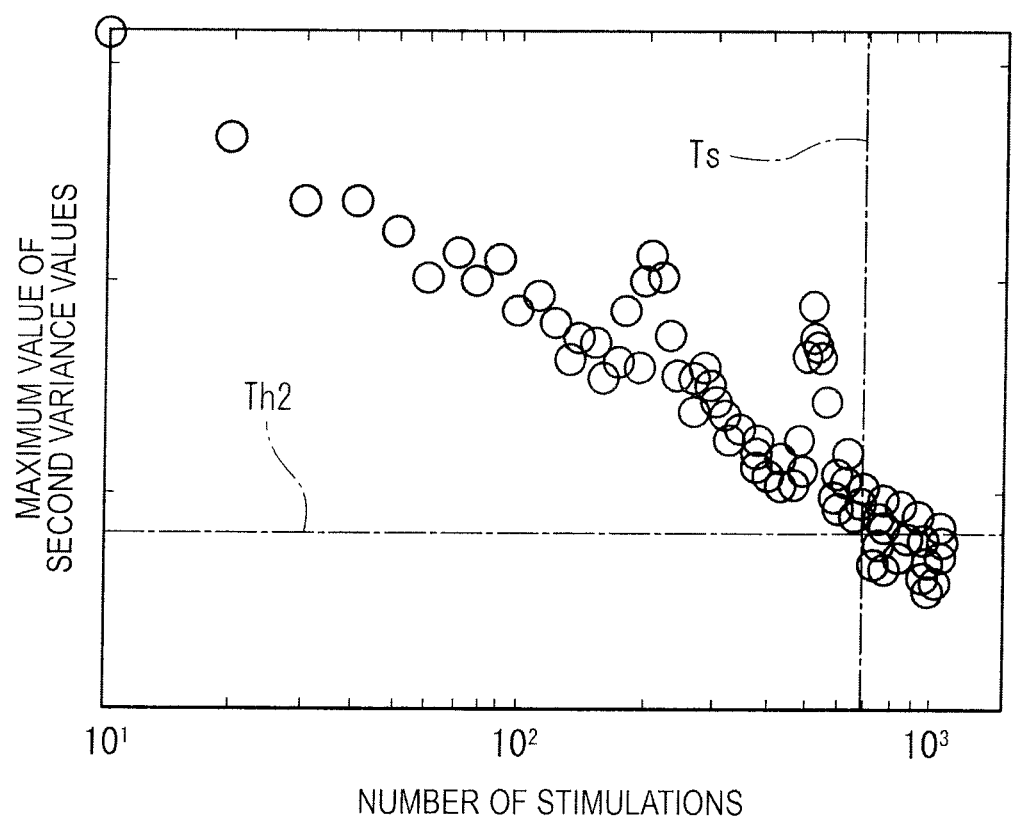
FIG. 4 is a view illustrating processes which are executed by the evoked potential measuring apparatus of FIG. 1.

The operation of the thus configured evoked potential measuring apparatus 1 will be described with reference to FIGS. 2 and 4. FIG. 4 illustrates relationships between the number of stimulations applied to the subject 2, and the maximum value of the second variance values calculated by the second variance value calculator 16. The abscissa indicates the number of stimulations which are applied to the subject 2, and the ordinates indicates the maximum value of the second variance values.

As indicated by the broken lines in FIG. 2, the second variance value calculator 16 calculates the second variance value with respect to the average waveform which is currently acquired by the average processing section 12 (S9).

Next, the controller 17 determines whether the maximum value of the second variance values calculated by the second variance value calculator 16 is smaller than the second threshold or not (S10). The dash-dot line Th2 in FIG. 4 indicates the second threshold. The second threshold is empirically determined as a variance value that is as small as that at which a significant evoked potential waveform can be determined.

If it is determined that the maximum value of the second variance values calculated by the second variance value calculator 16 is smaller than the second threshold (YES in step S10), the acquisition of evoked potential waveforms by the evoked potential acquiring section 11 is automatically stopped, and the measurement of an evoked potential is ended (S11). The dash-dot line Ts in FIG. 4 indicates the timing when the automatic stopping process is performed by the controller 17.

According to the configuration, while a significant evoked potential waveform is acquired from the subject 2, it is possible to prevent a situation where an unnecessary evoked potential measurement is continued by a subjective determination of the user, from occurring. Unnecessary stimulation application can be avoided. In an evoked potential measurement in which the arithmetic average method is used, therefore, the measurement can be performed highly accurately while the burden on the subject 2 is reduced.

Alternatively, the controller 17 may be configured so as to, if it is determined that the maximum value of the plurality of second variance values calculated by the second variance value calculator 16 is smaller than the predetermined second threshold, change the manner of displaying the average waveform on the displaying section 13.

As indicated by the broken lines in FIG. 2, if it is determined that the maximum value of the second variance values calculated by the second variance value calculator 16 is smaller than the second threshold (YES in step S10), specifically, the manner of displaying the average waveform on the displaying section 13 is changed (S12). Examples of the change of the display manner are a change of the color of at least one of the average waveform and the background screen, and a display of a notification symbol. The dash-dot line Ts in FIG. 4 indicates the timing when such a change of the display manner is performed.

Unlike the above-described example, the measurement of an evoked potential is not automatically ended, and the process transfers to the determination whether the ending conditions are satisfied or not (S8). If it is determined that the ending conditions are satisfied (YES in step S8), the evoked potential measurement is ended. If it is determined that the ending conditions are not satisfied (NO in step S8), the process returns to step S1, and the above-described processes are repeated in order to acquire the next waveform set.

According to the configuration, at a timing when a significant evoked potential waveform is acquired from the subject 2, it is possible to encourage the user to stop the evoked potential measurement. Unnecessary stimulation application can be avoided. In an evoked potential measurement in which the arithmetic average method is used, therefore, the measurement can be performed highly accurately while the burden on the subject 2 is reduced.

In addition to or in place of the above-described functions, the controller 17 may be configured so as to determine whether the maximum value of the plurality of first variance values calculated by the first variance value calculator 14 exceeds the first threshold or not. The controller 17 may be further configured so as to, if it is determined that the maximum value exceeds the first threshold, change the manner of displaying the average waveform on the displaying section 13.

As indicated by the broken line in FIG. 2, if it is determined that the maximum value of the plurality of first variance values calculated by the first variance value calculator 14 exceeds the first threshold (YES in step S6), specifically, the controller 17 changes the manner of displaying the average waveform on the displaying section 13 (S13). Examples of the change of the display manner are a change of the color of at least one of the average waveform and the background screen, and a display of a notification symbol.

According to the configuration, the user can be informed of the execution of the process of eliminating a waveform set which is affected by noises, from the arithmetic average. The process which is performed without involving consciousness is visualized, and therefore the user can be provided with a sense of safety due to the execution of the process which can reduce the burden on the subject 2.

As indicated by the broken lines in FIG. 1, the evoked potential measuring apparatus 1 may include a threshold determining section 18. The threshold determining section 18 is configured so as to determine the first threshold based on the maximum value of a predetermined number of first valiance values calculated by the first variance value calculator 14.

As indicated by the broken lines in FIG. 2, specifically, the threshold determining section 18 determines whether the number of times when the maximum value of the first variance values is calculated by the first variance value calculator 14 is equal to or larger than M (S14). For example, M is 3. In the case where N is 10, and M is 3, the above means that it is determined whether 3 waveform sets containing evoked potential waveforms up to the 30-th one after the start of the measurement are obtained or not.

If it is determined that the number of times when the maximum value of the first variance values is calculated is not larger than M (NO in step S14), the process returns to step S1, and the above-described processes are repeated in order to acquire the next waveform set. If it is determined that the number of times when the maximum value of the first variance values is calculated reaches M (YES in step S14), the threshold determining section 18 determines the first threshold based on the M number of maximum values of the first variance values (S15).

The manner of determining the first threshold may be adequately determined in accordance with the specifications. For example, the average value of the M number of maximum values of the first variance values is calculated, and the average value is multiplied by a predetermined coefficient, whereby the first threshold may be determined.

The characteristics of the evoked potential waveforms which are acquired from the subject 2 by the evoked potential acquiring section 11 vary among individuals. According to the above-described configuration, the first threshold is determined based on variance values calculated from the M×N number of evoked potential waveforms which are acquired from each subject 2, and a waveform set which is to be eliminated from the arithmetic average is determined based on this first threshold. Accordingly, a more dynamic and flexible process according to the subject 2 is enabled, and a significant average waveform can be acquired in a short period of time and highly accurately. In an evoked potential measurement in which the arithmetic average method is used, therefore, an accurate measurement can be performed while the burden on the subject 2 is reduced.

In the embodiment, the functions of the average processing section 12, the first variance value calculator 14, the updation processing section 15, the second variance value calculator 16, the controller 17, and the threshold determining section 18 are realized from software executed by a cooperation of a processor and memory which are communicably connected to each other. Examples of the processor are a CPU and an MPU. Examples of the memory are a RAM and a ROM. However, the function of at least one of the average processing section 12, the first variance value calculator 14, the updation processing section 15, the second variance value calculator 16, the controller 17, and the threshold determining section 18 may be realized by hardware such as circuit devices, or a combination of hardware and software.

Figure 5:
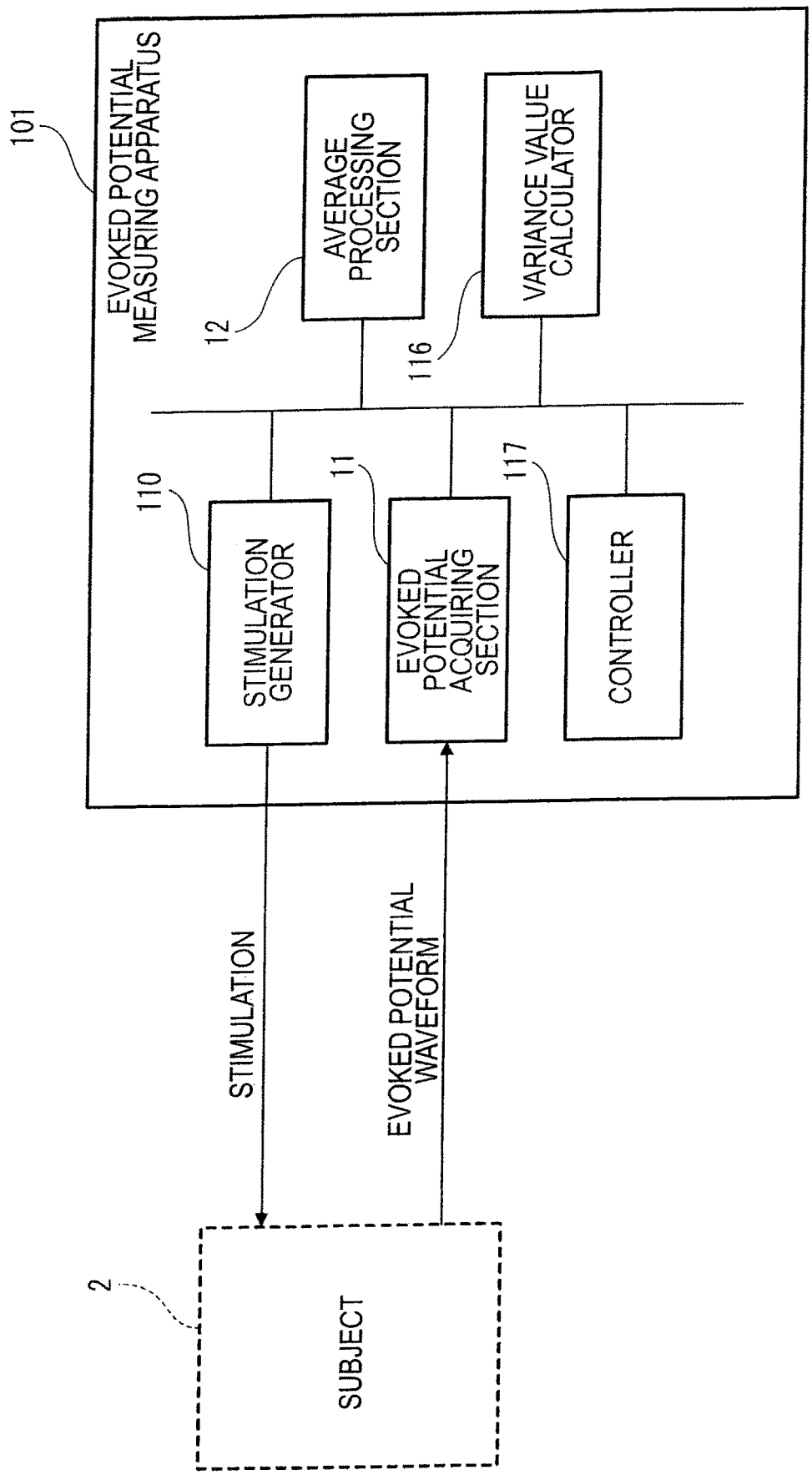
FIG. 5 is a block diagram illustrating the functional configuration of an evoked potential measuring apparatus of a second embodiment.

Next, an evoked potential measuring apparatus 101 of a second embodiment will be described with reference to FIG. 5. Components which are substantially identical with those of the evoked potential measuring apparatus 1 of the first embodiment are denoted by the same reference numerals, and duplicated descriptions are omitted.

The evoked potential measuring apparatus 101 may include a stimulation generator 110. The stimulation generator 110 is configured so as to generate stimulation which is to be applied to the subject 2. Examples of stimulation are visual stimulation, auditory stimulation, and pain stimulation. The stimulation generator 110 may be disposed in the evoked potential measuring apparatus 101, or outside the evoked potential measuring apparatus 101.

The evoked potential measuring apparatus 101 may include a variance value calculator 116 (an example of the statistical value calculator). The variance value calculator 116 is configured so as to calculate a variance value (an example of the statistical value) of the average waveform acquired by the average processing section 12. For example, the variance value is calculated in the following manner. An average waveform is expressed as a set of potential values at an X number of timings. For example, X is 1,000. A Y number of timings are selected from the X number of timings, and the variance values of potential values at the Y number of timings are calculated with respect to all evoked potential waveforms which have been added hitherto. For example, Y is 10 or 100.

The evoked potential measuring apparatus 101 may include a controller 117. The controller 117 is configured so as to determine whether the maximum value of the plurality of variance values calculated by the variance value calculator 116 is smaller than a predetermined threshold or not. If it is determined that the maximum value is smaller than the threshold, the controller 117 causes the stimulation generation by the stimulation generator 110, to be automatically stopped.

According to the configuration, while a significant evoked potential waveform is acquired from the subject 2, it is possible to prevent a situation where an unnecessary evoked potential measurement is continued by a subjective determination of the user, from occurring. Unnecessary stimulation application can be avoided. In an evoked potential measurement in which the arithmetic average method is used, therefore, the measurement can be performed highly accurately while the burden on the subject 2 is reduced.

In the embodiment, the functions of the average processing section 12, the variance value calculator 116, and the controller 117 are realized from software executed by a cooperation of a processor and memory which are communicably connected to each other. Examples of the processor are a CPU and an MPU. Examples of the memory are a RAM and a ROM.

However, the function of at least one of the average processing section 12, the variance value calculator 116, and the controller 117 may be realized by hardware such as circuit devices, or a combination of hardware and software.

Figure 6:
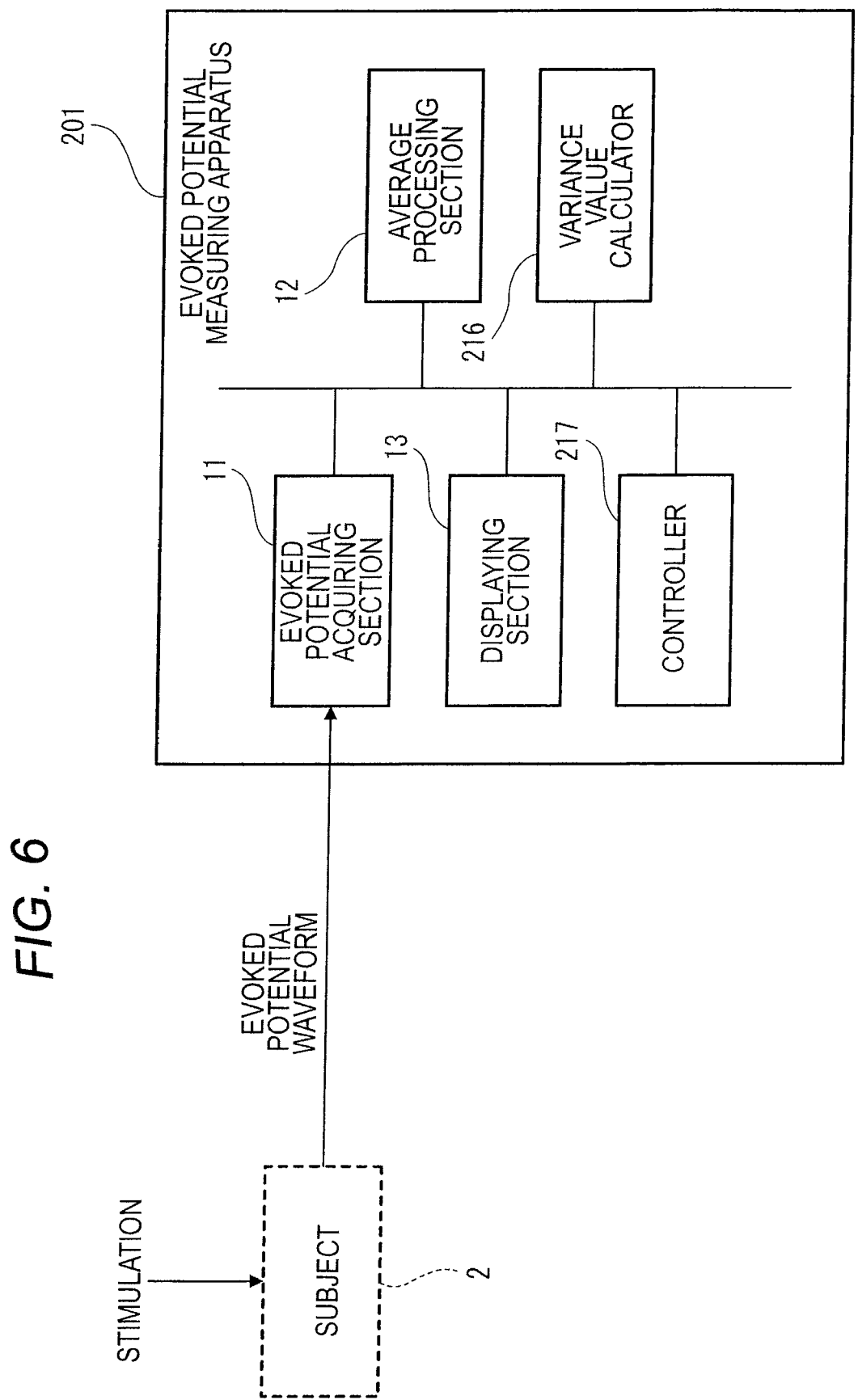
FIG. 6 is a block diagram illustrating the functional configuration of an evoked potential measuring apparatus of a third embodiment.

Next, an evoked potential measuring apparatus 201 of a third embodiment will be described with reference to FIG. 6. Components which are substantially identical with those of the evoked potential measuring apparatus 1 of the first embodiment are denoted by the same reference numerals, and duplicated descriptions are omitted.

The evoked potential measuring apparatus 201 may include a variance value calculator 216 (an example of the statistical value calculator). The variance value calculator 216 is configured so as to calculate a variance value (an example of the statistical value) of the average waveform acquired by the average processing section 12. For example, the variance value is calculated in the following manner. An average waveform is expressed as a set of potential values at an X number of timings. For example, X is 1,000. A Y number of timings are selected from the X number of timings, and the variance values of potential values at the Y number of timings are calculated with respect to all evoked potential waveforms which have been added hitherto. For example, Y is 10 or 100.

The evoked potential measuring apparatus 201 may include a controller 217. The controller 217 is configured so as to determine whether the maximum value of the plurality of variance values calculated by the variance value calculator 216 is smaller than a predetermined threshold or not. If it is determined that the maximum value is smaller than the threshold, the controller 217 causes the manner of displaying the average waveform on the displaying section 13, to be changed. Examples of the change of the display manner are a change of the color of at least one of the average waveform and the background screen, and a display of a notification symbol.

According to the configuration, at the timing when a significant evoked potential waveform is acquired from the subject 2, it is possible to encourage the user to stop the evoked potential measurement. Unnecessary stimulation application can be avoided. In an evoked potential measurement in which the arithmetic average method is used, therefore, the measurement can be performed highly accurately while the burden on the subject 2 is reduced.

In the embodiment, the functions of the average processing section 12, the variance value calculator 216, and the controller 217 are realized from software executed by a cooperation of a processor and memory which are communicably connected to each other. Examples of the processor are a CPU and an MPU. Examples of the memory are a RAM and a ROM. However, the function of at least one of the functions of the average processing section 12, the variance value calculator 216, and the controller 217 may be realized by hardware such as circuit devices, or a combination of hardware and software.

The above-described embodiments are mere examples for facilitating understanding of the presently disclosed subject matter. The configurations of the embodiments may be adequately changed or improved without departing the spirit of the presently disclosed subject matter. It is obvious that equivalents are included within the technical scope of the presently disclosed subject matter.

In the above-described embodiments, the maximum value of variance values is exemplified as the statistical value which is calculated based on evoked potential waveforms acquired from the subject 2. However, various statistical values may be employed in accordance with the specifications. For example, the average value, standard deviation value, unbiased variance value, expected value, or correlation coefficient of variance values may be employed. Alternatively, the statistical value may be obtained based on the latencies of response or areas under waveform of evoked potential waveforms which are acquired in response to stimulation.

According to an aspect of the presently disclosed subject matter, there is provided an evoked potential measuring apparatus comprising: an evoked potential acquiring section which is configured to acquire a plurality of evoked potential waveforms from a subject in response to stimulation; an average processing section which is configured to arithmetically average the plurality of evoked potential waveforms to acquire an average waveform; a first statistical value calculator which, each time a waveform set including an N (N is 2 or more) number of evoked potential waveforms is acquired, is configured to calculate a first statistical value of the waveform set; and an updation processing section which is configured to update the average waveform to eliminate a waveform set in which the first statistical value exceeds a first threshold, from the arithmetic average.

In the case where a waveform set in which the first statistical value exceeds the first threshold is acquired, it is highly probable that, at the timing when the waveform set is acquired, noises which are hardly eliminated by the arithmetic averaging are added to the waveform set. When such a waveform set remains as a component of the average waveform, a substantial time period is required to acquire a significant average waveform. According to the configuration, such a waveform set is eliminated from the arithmetic average, whereby the average waveform can be returned to the state attained before the problematic noises are mixed into the waveform. Therefore, the time period which elapses until a significant average waveform is acquired can be shortened, and namely the number of times when stimulation is applied to the subject can be reduced. In an evoked potential measurement in which the arithmetic average method is used, therefore, the measurement can be performed highly accurately while the burden on the subject is reduced.

According to an aspect of the presently disclosed subject matter, there is also provided an evoked potential measuring apparatus comprising: a stimulation generator which is configured to generate stimulation that is to be applied to a subject; an evoked potential acquiring section which is configured to acquire a plurality of evoked potential waveforms from the subject in response to the simulation; an average processing section which is configured to arithmetically average the plurality of evoked potential waveforms to acquire an average waveform; a statistical value calculator which is configured to calculate a statistical value of the average waveform; and a controller which, when the statistical value is smaller than a threshold, is configured to cause the generation of the stimulation to be automatically stopped.

According to the configuration, while a significant evoked potential waveform is acquired from the subject, it is possible to prevent a situation where an unnecessary evoked potential measurement is continued by a subjective determination of the user, from occurring. Unnecessary stimulation application can be avoided. In an evoked potential measurement in which the arithmetic average method is used, therefore, the measurement can be performed highly accurately while the burden on the subject is reduced. Moreover, the measurement is ended at the timing when an appropriate result is obtained, and therefore the measurement time period can be shortened.

According to an aspect of the presently disclosed subject matter, there is provided an evoked potential measuring apparatus comprising: an evoked potential acquiring section which is configured to acquire a plurality of evoked potential waveforms from a subject in response to stimulation; an average processing section which is configured to arithmetically average the plurality of evoked potential waveforms to acquire an average waveform; a displaying section which is configured to display the average waveform; a statistical value calculator which is configured to calculate a statistical value of the average waveform; and a controller which, when the statistical value is smaller than a threshold, is configured to cause a manner of displaying the average waveform on the displaying section, to be changed.

According to the configuration, at the timing when a significant evoked potential waveform is acquired from the subject, it is possible to encourage the user to stop the evoked potential measurement. Unnecessary stimulation application can be avoided. In an evoked potential measurement in which the arithmetic average method is used, therefore, the measurement can be performed highly accurately while the burden on the subject is reduced.

What is claimed is:

1. An evoked potential measuring apparatus comprising: at least one processor and memory configured to:
    arithmetically average a plurality of evoked potential waveforms thereby acquiring an average waveform, the plurality of evoked potential waveforms being acquired form a subject in response to stimulation;
    calculate a first statistical value of acquired evoked potentials for at least two waveform sets, the at least two waveform sets each including at least two of the plurality of acquired evoked potential waveforms;
    calculate second statistical values of the average waveform;
    determine whether a number of times the first statistical value is calculated is equal to or greater than a first predetermined number;
    when the number of times the first statistical value is calculated is equal to or greater than the first predetermined number, determine a first threshold based on the first predetermined number of first statistical values;
    when the first statistical value of one of the waveform sets exceeds the first threshold, update the average waveform to eliminate the one waveform set from the average waveform; and
    when a maximum of the calculated second statistical values is smaller than a second threshold and a number of the plurality of evoked potential waveforms is equal to or greater than a second predetermined number, cause acquisition of the evoked potential waveforms to be automatically stopped, wherein the second predetermined number is greater than a number of evoked potential waveforms that are used to calculate the first statistical value; and
    a display configured to display the updated average waveform.

2. The evoked potential measuring apparatus according to claim 1, wherein when one of the second statistical values is smaller than the second threshold, the display changes a manner of displaying the average waveform.

3. The evoked potential measuring apparatus according to claim 1, wherein when the first statistical value exceeds the first threshold, the display changes a manner of displaying the average waveform.

4. The evoked potential measuring apparatus according to claim 1, wherein the first statistical value is a variance value, a standard deviation value, an unbiased variance value, an expected value, or a correlation coefficient.

5. The evoked potential measuring apparatus according to claim 1, wherein the second statistical values are variance values, standard deviation values, unbiased variance values, expected values, or correlation coefficients.

6. The evoked potential measuring apparatus according to claim 1, wherein the processor and memory are further configured to determine the first threshold by calculating an average of the first predetermined number of first statistical values, and multiplying the average of the first statistical values by a predetermined coefficient.

7. The evoked potential measuring apparatus according to claim 1, where the second statistical values are variance values of portions of the average waveform.

* * * * *